(12) United States Patent
Simon

(10) Patent No.: US 8,480,634 B2
(45) Date of Patent: Jul. 9, 2013

(54) PRESSURE COMPENSATING DEVICE

(76) Inventor: Michael G. Simon, Del Mar, CA (US)

( * ) Notice: Subject to any disclaimer, the term of this patent is extended or adjusted under 35 U.S.C. 154(b) by 76 days.

(21) Appl. No.: 12/322,476

(22) Filed: Feb. 3, 2009

(65) Prior Publication Data

US 2010/0198154 A1    Aug. 5, 2010

(51) Int. Cl.
 *A61M 5/00*    (2006.01)
(52) U.S. Cl.
 USPC ........................................................ 604/246
(58) Field of Classification Search
 USPC ................... 604/246, 247, 533–538; 137/843
 See application file for complete search history.

(56) References Cited

U.S. PATENT DOCUMENTS

| | | | |
|---|---|---|---|
| 3,207,641 A | 9/1965 | Simko, Jr. et al. | |
| 3,532,126 A | 10/1970 | Boothe | |
| 3,620,500 A | 11/1971 | Santomieri | |
| 3,656,138 A | 4/1972 | Hamma | |
| 3,785,378 A | 1/1974 | Stewart | |
| 3,806,086 A | 4/1974 | Cloyd | |
| 3,841,354 A | 10/1974 | McDonnell | |
| 3,868,973 A | 3/1975 | Bierman et al. | |
| 3,957,082 A | 5/1976 | Fuson et al. | |
| 4,079,737 A | 3/1978 | Miller | |
| 4,146,055 A | 3/1979 | Ryder et al. | |
| 4,300,552 A | 11/1981 | Cannon | |
| 4,361,147 A | 11/1982 | Aslanian et al. | |
| 4,384,680 A | 5/1983 | Mehoudar | |
| 4,415,003 A * | 11/1983 | Paradis et al. | 137/843 |
| 4,474,574 A | 10/1984 | Wolfe et al. | |
| 4,504,263 A | 3/1985 | Steuer et al. | |
| 4,515,588 A | 5/1985 | Amendolia | |
| 4,533,348 A | 8/1985 | Wolfe et al. | |
| 4,581,014 A | 4/1986 | Millerd et al. | |
| 4,589,872 A | 5/1986 | Bellin et al. | |
| 4,593,717 A | 6/1986 | Levasseur | |
| 4,604,093 A | 8/1986 | Brown | |
| 4,613,325 A | 9/1986 | Abrams | |
| 4,634,434 A | 1/1987 | Marino, Jr. et al. | |
| 4,722,732 A | 2/1988 | Martin | |
| 4,738,665 A | 4/1988 | Shepard | |
| 4,769,012 A | 9/1988 | Quang et al. | |
| 4,789,000 A | 12/1988 | Aslanian | |
| 4,802,506 A | 2/1989 | Aslanian | |
| 4,807,660 A | 2/1989 | Aslanian | |
| 4,822,344 A | 4/1989 | O'Boyle | |
| 4,874,386 A | 10/1989 | O'Boyle | |
| 4,917,687 A | 4/1990 | O'Boyle | |
| 4,925,451 A | 5/1990 | Amendolia | |
| 4,947,856 A | 8/1990 | Beard | |
| 5,005,604 A | 4/1991 | Aslanian | |
| 5,009,251 A | 4/1991 | Pike et al. | |

(Continued)

OTHER PUBLICATIONS

3M Health Care brochure, "3M IV Flow Regulator Sets" (1993), 4 pages.

(Continued)

*Primary Examiner* — Theodore Stigell
*Assistant Examiner* — Jenna Zhang
(74) *Attorney, Agent, or Firm* — Kinney & Lange, P.A.

(57) ABSTRACT

A pressure compensating device includes a compensating disc located within an internal chamber of a housing. The compensating disc has a diaphragm over which fluid passes after entering the internal chamber. The diaphragm deflects in response to a pressure differential between fluid entering the internal chamber and fluid exiting the internal chamber to maintain the set flow rate of the fluid.

16 Claims, 5 Drawing Sheets

U.S. PATENT DOCUMENTS

| | | |
|---|---|---|
| 5,014,750 A | 5/1991 | Winchell et al. |
| 5,033,714 A | 7/1991 | Winchell et al. |
| D319,506 S | 8/1991 | Lal et al. |
| 5,113,904 A | 5/1992 | Aslanian |
| 5,176,360 A | 1/1993 | Winchell et al. |
| 5,190,527 A | 3/1993 | Hamilton et al. |
| 5,234,413 A | 8/1993 | Wonder et al. |
| 5,240,035 A | 8/1993 | Aslanian et al. |
| 5,241,985 A | 9/1993 | Faust et al. |
| 5,346,477 A | 9/1994 | Edwards et al. |
| 5,413,282 A | 5/1995 | Boswell |
| 5,445,622 A | 8/1995 | Brown |
| 5,499,968 A | 3/1996 | Milijasevic |
| 5,520,661 A * | 5/1996 | Lal et al. .................. 604/246 |
| 5,730,730 A | 3/1998 | Darling, Jr. |
| 6,213,986 B1 | 4/2001 | Darling, Jr. |
| 6,290,681 B1 | 9/2001 | Brown |
| 6,709,417 B1 | 3/2004 | Houle et al. |
| 2003/0135164 A1* | 7/2003 | Simon .......................... 604/246 |
| 2005/0065480 A1 | 3/2005 | Lee et al. |
| 2005/0131335 A1 | 6/2005 | Drott et al. |
| 2005/0197631 A1 | 9/2005 | Schinazi et al. |

OTHER PUBLICATIONS

PCT International Search Report and the Written Opinion of the International Searching Authority, Sep. 27, 2010, 14 pages.

\* cited by examiner

PRESSURE COMPENSATING DEVICE

BACKGROUND

Fluids and drugs are frequently administered to patients by intravenous infusion, also known as IV therapy. For IV therapy administration, a bag of IV solution is usually hung above a patient. Gravity pulls the IV solution downwards through a flexible line of delivery tubing to a venipuncture site on the patient, often in the forearm, wrist, or hand. To control the rate at which the IV solution is delivered to the patient, a pinch valve or roller clamp can be included on the outer surface of the tubing. Pinch valves and roller clamps compress the tubing to progressively restrict the flow of the IV solution reaching the patient's vein.

Even after a particular IV solution delivery rate is set with a pinch valve or roller clamp, substantial deviations in the flow rate can be observed. For example, as IV therapy progresses, the amount of IV solution remaining within the IV bag will be reduced. Along with this reduction in volume, the head pressure acting on the remaining IV solution is reduced and therefore, flow rate slows. Unwanted changes in flow rate can also by caused by changes in elevation of the IV bag or simple movement of a patient's limb. Indeed, Bernoulli's principle teaches that the total energy at a given point in a fluid is the energy associated with the movement of the fluid, plus energy from pressure in the fluid, plus energy from the height of the fluid relative to an arbitrary datum. Working knowledge of Bernoulli's principle, however, does not lead to a perfect pressure compensating device. Pressure head variations are unpredictable and remain difficult to manage in IV therapy administration.

SUMMARY

An embodiment of the present invention is a pressure compensating device including a housing and a compensating disc. The housing includes an inlet port, an outlet port fluidly connected to the inlet port, an annular land surrounding the outlet port and an internal chamber located between the inlet port and the outlet port. The compensating disc is located within the internal chamber and has a diaphragm with a centrally located flex point. The diaphragm engages the land allowing the flex point to flex freely above the outlet port.

Another embodiment of the present invention is a pressure compensating device including a housing and a compensating disc. The housing has an upper housing section and a lower housing section. An inlet extends from the upper housing and an outlet extends from the lower housing. An internal chamber is located between the upper housing and the lower housing. An inlet port is located in the upper housing fluidly connecting the inlet to the chamber and an outlet port is located in the lower housing fluidly connecting the outlet to the chamber. A port ring surrounds the outlet port and has a height. An annular land surrounds the port ring and has an upper surface, an outer diameter and a height. The compensating disc is located within the internal chamber. The compensating disc includes a thick outer rim. The rim has a top surface, a side surface, a bottom surface, a height, an inner diameter and an outer diameter. The compensating disc also includes a diaphragm that extends across the bottom surface to the outer diameter. The diaphragm has a top side, a bottom side and a centrally located flex point. The rim height relative to the land height, the inner diameter of the rim relative to the outer diameter of the land, and the annular land height relative to the port ring height are related such that the diaphragm engages and stretches across the land equally thereby bringing the flex point in alignment with a central axis of the outlet port.

DETAILED DESCRIPTION

Control over flow rate during administration of IV therapy requires use of a flow regulating device such as pinch valve or roller clamp. Pinch valves or roller clamps, however, fail to account for changes in fluid pressure. There exists a need for a pressure compensating device for use during administration of IV therapy.

Figure 1:
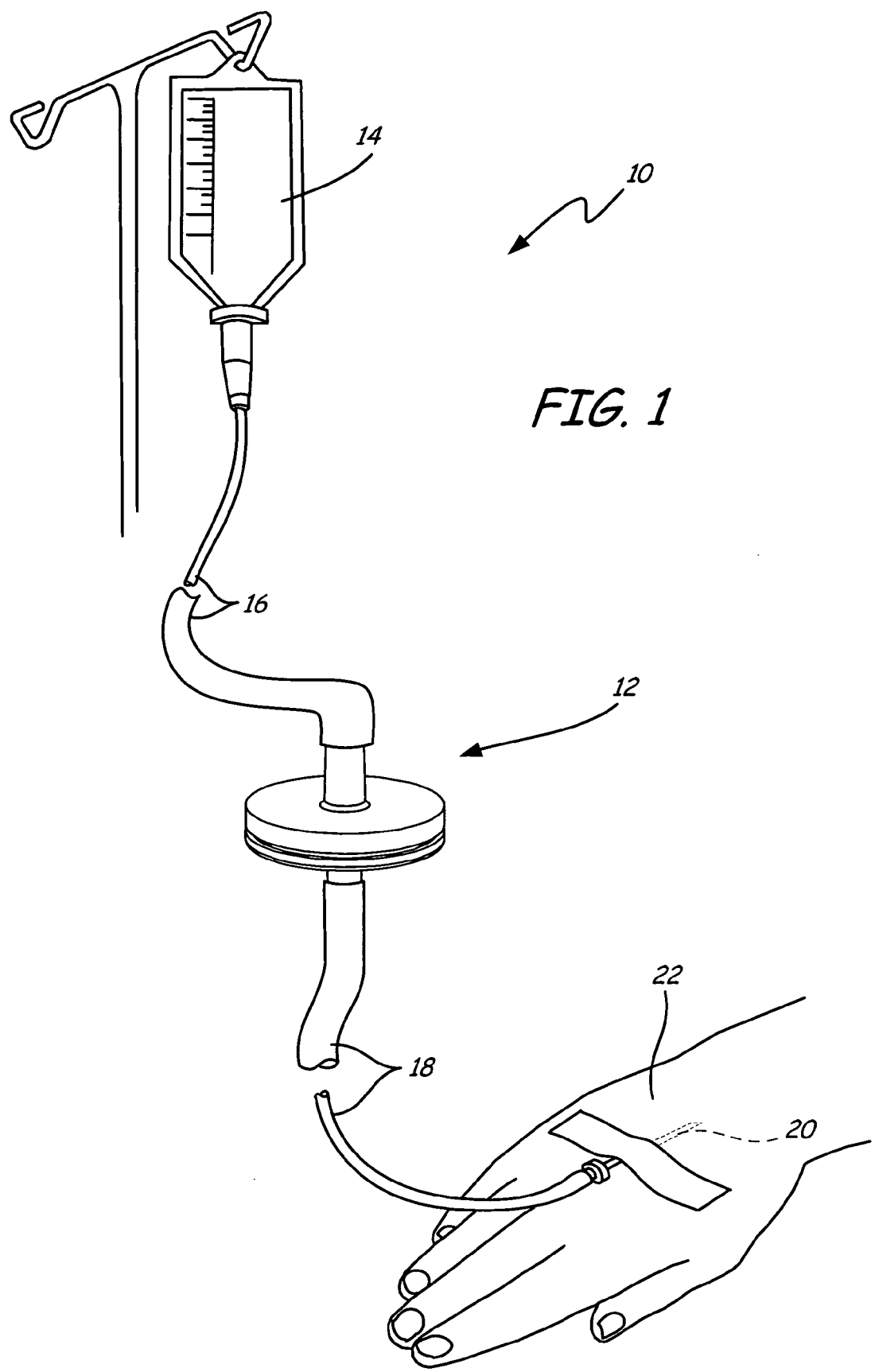
FIG. 1 is a schematic view of an IV therapy administration system including a pressure compensating device in accordance with the present invention.

FIG. 1 is a schematic view of IV therapy administration system 10 including pressure compensating device 12 in accordance with the present invention. Depicted in FIG. 1 are the components of IV therapy administration system 10: pressure compensating device 12, IV bag 14, upper tubing 16, lower tubing 18, venipuncture site 20, and patient 22. Pressure compensating device 12 compensates for variations in the head pressure of IV solution in IV therapy administration system 10.

Pressure compensating device 12 is located between IV bag 14 and venipuncture site 20. Fluidly connecting pressure compensating device 12 to IV bag 14 is flexible upper tubing 16. Similarly, flexible lower tubing 18 connects pressure compensating device 12 to venipuncture site 20 on patient 22. Located along upper tubing 16 or lower tubing 18, a flow control regulator, such as but not limited to a pinch valve or roller clamp, can be incorporated into IV therapy administration system 10. Venipuncture site 20 provides direct access to patient's 22 circulatory system via a needle inserted into a peripheral vein. To administer the contents of IV bag 14 to patient 22, IV bag 14 is hung above patient 22 with pressure compensating device 12 positioned between IV bag 14 and venipuncture site 20.

IV therapy administration system 10 uses gravity to pull an IV solution downwardly out of IV bag 14 through upper tubing 16 to pressure compensating device 12 through lower tubing 18 and into venipuncture site 20 on patient 22. Pressure compensating device 12 uses fluid head pressure exerted on IV solution in IV bag 14 to overcome the venous back pressure of patient 22. As IV therapy progresses, however, the volume of solution within IV bag 14 is reduced. The reduced volume changes head pressure in IV administration system 10, thereby slowing the rate at which IV solution is delivered to venipuncture site 20. Pressure compensating device 12 is configured to compensate for such variations in fluid pressure and maintain a predetermined flow rate.

Figure 2:
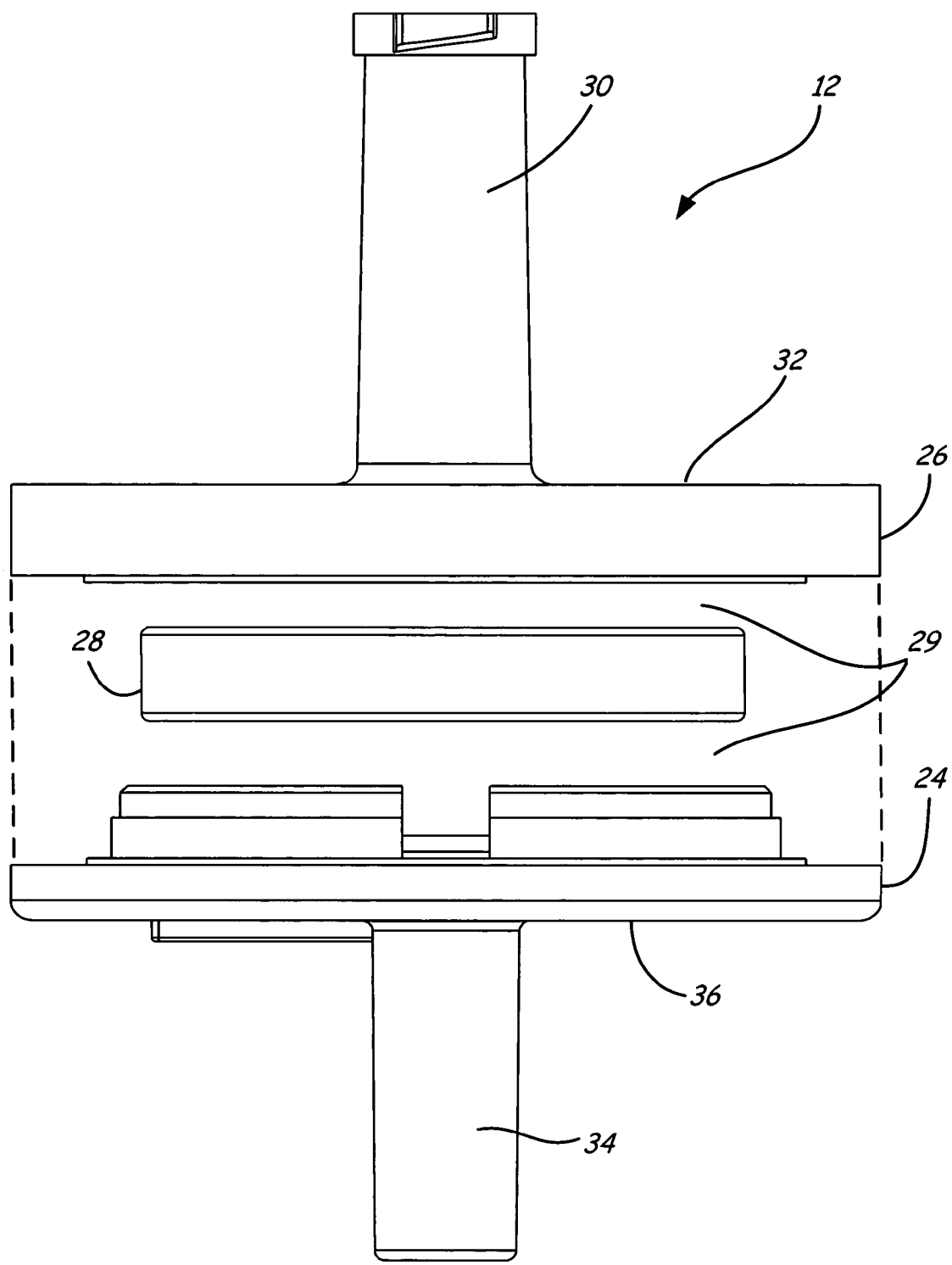
FIG. 2 is an exploded side view of pressure compensating device from FIG. 1.

FIG. 2 is an exploded side view of pressure compensating device from FIG. 1. Depicted in FIG. 2 are the components of pressure compensating device 12: lower housing 24, upper housing 26, compensating disc 28, internal chamber 29, inlet 30, top surface 32, outlet 34, and bottom surface 36. The components of pressure compensating device 12 are assembled to compensate for changes in fluid pressure within IV administration system 10.

Pressure compensating device 12 is constructed from lower housing 24 and upper housing 26. Lower housing 24 and upper housing 26 can be formed by injection molding of a suitable medical grade plastic material such as polypropylene. Just as the names indicate, lower housing 24 is located beneath and attached to upper housing 26. In between upper housing 26 and lower housing 24, is compensating disc 28. Compensating disc 28 can be formed by compression molding of a suitable medical grade material elastomer, such as silicone rubber. Upper housing 26 and lower housing 24 fit together to form internal chamber 29 above and below compensating disc 28. Attached to upper housing 26 is inlet 30. More specifically, inlet 30 extends at an approximately right angle from top surface 32 of upper housing 26. In opposition to inlet 30 is outlet 34 attached to lower housing 24. Outlet 30 extends at an approximately right angle from bottom surface 36 of lower housing 24. So assembled, the components of pressure compensating device 12 function together to maintain the set flow rate despite changes in fluid pressure between inlet 30 and outlet 34.

IV solution enters pressure compensating device 12 via inlet 30 on upper housing 26. Upon entering internal chamber 29, fluid encounters compensating disc 28. A top surface of compensating disc 28 is at essentially the same pressure as IV fluid within IV bag 14, whereas a bottom surface of compensating disc 28 is at essentially the same pressure as venipuncture site 20. If pressure exerted on the top surface of compensating disc 28 is reduced, compensating disc 28 will flex away from lower housing 24 effectively increasing the effective size of an outlet port on lower housing 24. A larger outlet port increases the rate of fluid flow out of outlet 34. The converse is also true such that an increase in top surface pressure results in compensating disc 28 flexing toward an outlet port on lower housing 24 thereby decreasing rate of fluid flow through lower housing 24 and out of outlet 34. Compensating disc 28, therefore, flexes toward or flexes away from an outlet port to compensate for changes in fluid pressure. The components of pressure compensating device 12 are discussed individually and in further detail below.

Lower Housing 24

Figure 3:
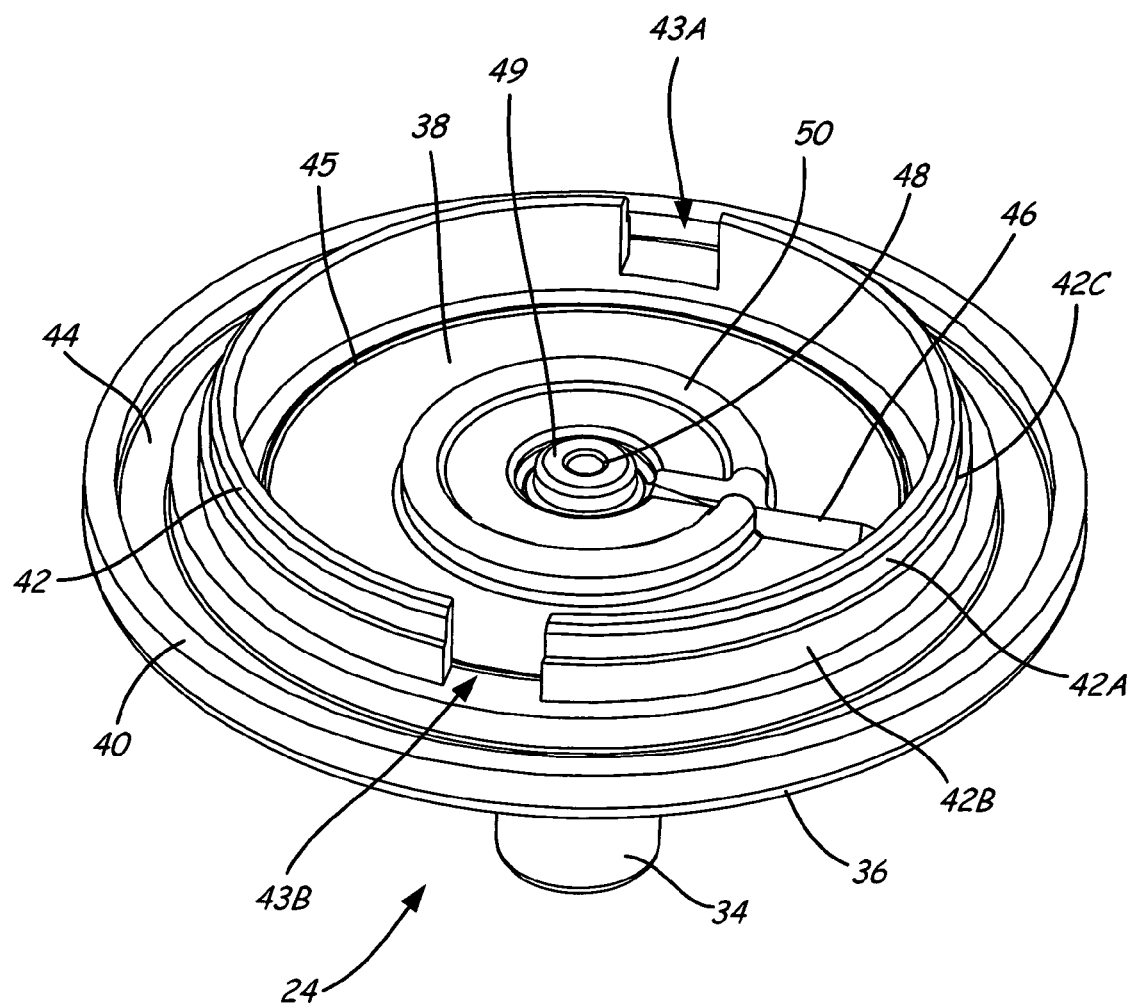
FIG. 3 is a top perspective view of the lower housing from FIG. 2.

FIG. 3 is a top perspective view of lower housing 24 from FIG. 2. Depicted in FIG. 3 are the components of lower housing 24: outlet 34, bottom surface 36, top surface 38, rim 40, flange 42, notches 43, track 44, sealing ring 45, channel 46, outlet port 48, outlet port ring 49, and land 50. Lower housing 24 is configured to form a bottom portion of internal chamber 29, which holds compensating disc 28.

Lower housing 24 has a bottom surface 36 and an opposing top surface 38. Extending downwardly from an approximate center of bottom surface 36 is outlet 34. In the depicted embodiment, outlet 34 forms an approximately right angle with bottom surface 36 of lower housing 24, and is sized to receive medical tubing, such as lower tubing 18. The circumference of lower housing 24 is defined by rim 40, which protrudes upwardly from top surface 38 of lower housing 24. Within rim 40 and also extending upwardly from top surface 38 is flange 42. Flange 42 includes upper portion 42A, lower portion 42B, and shoulder 42C located between upper portion 42A and lower portion 42B. Although flange 42 is mostly continuous and annular, one or more cut-outs or notches 43 can extend into flange 42. In the embodiment depicted, two notches 43A and 43B are shown. Between rim 40 and flange 42 is annular track 44, which also extends around the top surface of lower housing 24. Inside of, and immediately adjacent to flange 42, is sealing ring 45. Sealing ring 45, like track 44, is annular and continuous around top surface 38 of lower housing 24. In the embodiment depicted, sealing ring 45 has a height between approximately 0.005 and 0.015 inches (0.0127 and 0.0381 centimeters) and a width between approximately 0.015 and 0.025 inches (0.0381 and 0.0635 centimeters), although the invention is not so limited. Sealing ring 45 can assume any configuration capable of maintaining a proper seal with compensating disc 28. Located within sealing ring 45 is radial channel 46 extending from a location near sealing ring 45 to centrally located outlet port 48. Outlet port 48 leads fluid from channel 46 into outlet 34 and therefore, out of compensating device 12. Also within sealing ring 45 and extending around outlet port 48 is raised port ring 49. Between port ring 49 and sealing ring 45 is raised land 50. Land 50 is substantially annular and convex except for a small cut-out where channel 46 is connected to outlet port 48 to allow for fluid connection.

Lower housing 24 is the lowermost portion of compensating device 12. Outlet 34 is the location where fluid is discharged from flow rate regulator 12, usually into lower tubing 18 for administration to patient 22. Upwardly extending rim 40, flange 42, notches 43A and 43B, and track 44 are all configured to couple with corresponding mating parts depending downwardly from upper housing 26. Once assembled, fluid exiting upper housing 26 arrives on a top surface of compensating disc 28, which rests centrally on top surface 38 within flange 42. More specifically, compensating disc 28 engages sealing ring 45 and land 50 of lower housing 24. Sealing ring 45 functions to prevent fluid from leaking out of lower housing 24 and also secures compensating disc 28 onto lower housing 24. Compensating disc 28 engages or stretches across land 50 so that it is sufficiently taut to allow flexing or oscillation above outlet port 48. Once fluid flows over a top surface and around a side surface of compensating disc 28, fluid arrives at channel 46 of lower housing 24. From channel 46, fluid is directed inwards toward outlet port 48. Outlet port 48 is fluidly connected to outlet 34 where fluid is discharged from compensating device 12. So assembled, lower housing 24 engages compensating disc 28, which flexes in response to changes in fluid pressure.

Compensating Disc 28

Figure 4:
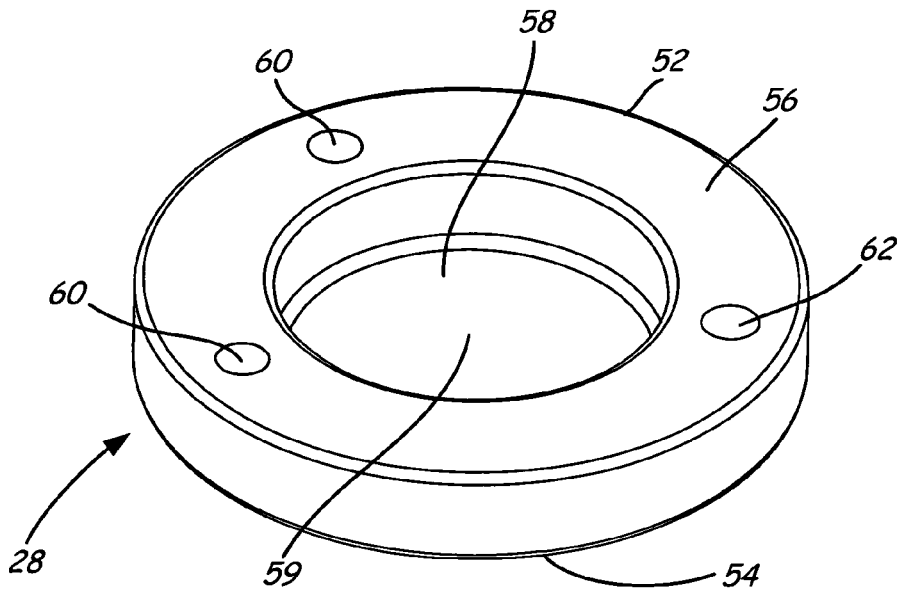
FIG. 4 is a top perspective view of the compensating disc from FIG. 2.

FIG. 4 is a top perspective view of compensating disc 28 from FIG. 2. Depicted in FIG. 4 are the components of compensating disc 28: top surface 52, bottom surface 54, rim 56, diaphragm 58, flex point 59, holes 60, and through bore 62. Diaphragm 58 flexes to compensate for a difference in fluid pressure between inlet 30 and outlet 34.

Compensating disc 28 has top surface 52 and opposing bottom surface 54. Thick annular rim 56 extends around a circumference of compensating disc 28. Extending across bottom surface 54 of annular rim 56 is diaphragm 58. Diaphragm 58 attaches to an outer diameter of, and is integral with, rim 56. Centrally located within diaphragm 58 is flex point 59. Two holes 60 are shown extending into rim 56, although more or less holes 60 are possible. One through bore 62 is also shown extending all the way through rim 56, although more or less bores 62 are possible. Holes 60 are configured to precisely align disc 28 to mating upper housing 26 such that through bore 62 is precisely centered under flow channel outlet 82B (shown in FIG. 5).

When assembled into compensating device 12, compensating disc 28 is located in internal chamber 29 formed between upper housing 26 and lower housing 24. So placed, at least a portion of top surface 52 contacts upper housing 26. Similarly, at least a portion of bottom surface 54 contacts lower housing 24. More specifically, bottom surface of diaphragm 58 contacts an outer diameter and top surface of land 50 on lower housing 24. Bottom surface of diaphragm 58 stretches up and over land 50 so that diaphragm 58 is slightly taut. When diaphragm 58 is stretched over land 50, flex point 59 is aligned over a central axis of outlet port 48. Flex point 59 of diaphragm 58 is configured to flex or deflect toward and away from port ring 49 in response to changes in fluid pressure. Holes 60 mate with locator pins 74 projecting from upper housing 26 to align through bore 62 with flow channel outlet 82B, located on upper housing 26. Through bore 62 then provides a fluid connection between upper housing 26 and lower housing 24. The arrangement of compensating disc 28 with respect to upper housing 26 is discussed further with reference to FIG. 5.

Figure 5:
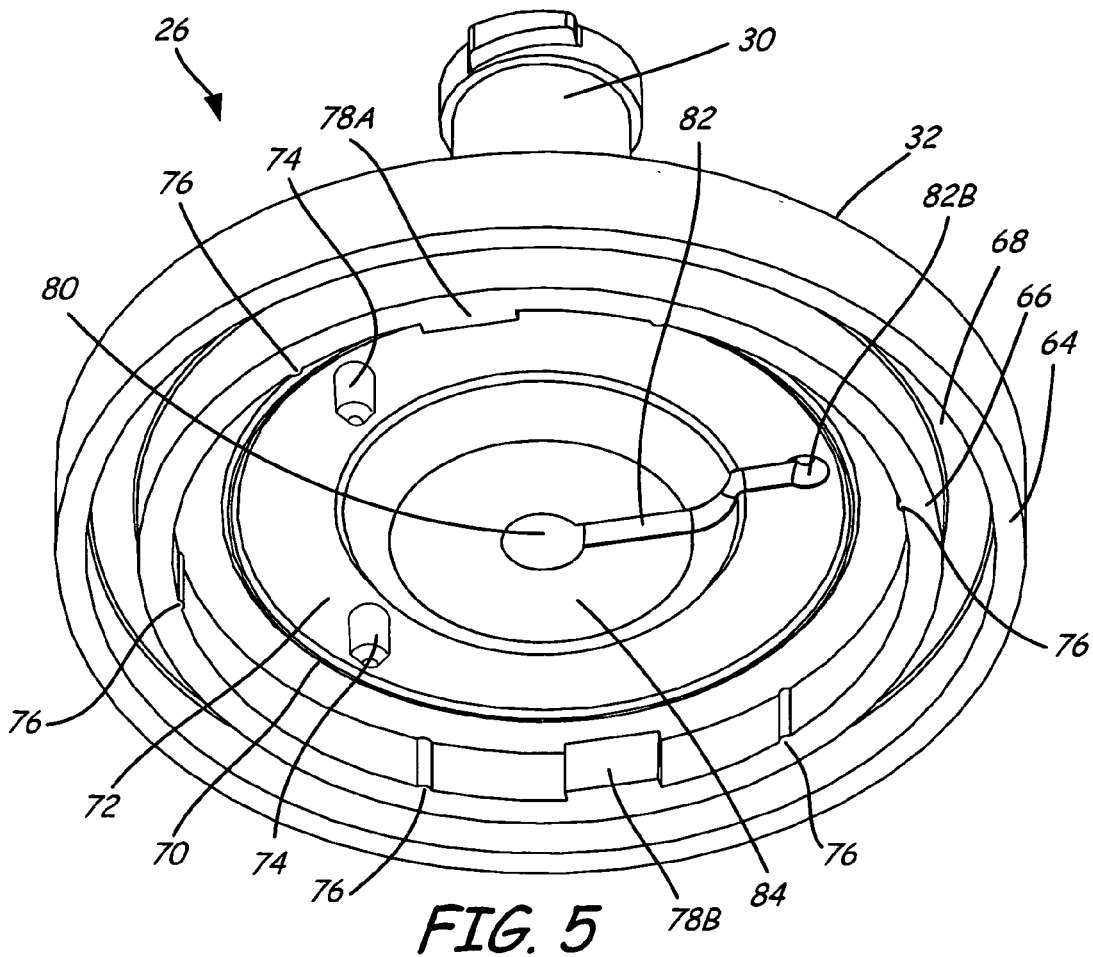
FIG. 5 is a bottom perspective view of the upper housing from FIG. 2.

FIG. 5 is a bottom perspective view of upper housing 26 from FIG. 2. Depicted in FIG. 5 are the components of upper housing 26 as seen from the bottom: inlet 30, top surface 32, outer lip 64, inner lip 66, track 68, sealing ring 70, bottom surface 72, locator pins 74, centering ribs 76, tabs 78, inlet port 80, flow channel 82, and puck 84. Upper housing 26 mates with lower housing 24 to create internal chamber 29, which houses compensating disc 28.

Upper housing 26 has inlet 30 extending from an approximate center of top surface 32. Inlet 30 extends outwardly and upwardly from top surface 32 of upper housing 26 at an angle of approximately 90 degrees. In the embodiment depicted, inlet 30 is circular in cross-section and sized to be connectable to conventional medical tubing, such as upper tubing 16. Inlet 30 defines an inlet passage for receiving liquid that fluidly connects inlet port 80 to flow channel 82. Facing in the opposite direction from top surface 32 is bottom surface 72. Extending downwardly from bottom surface 72 are outer lip 64 and inner lip 66. Both inner lip 66 and outer lip 64 are annular and continuous. Outer lip 64 depends from the periphery of upper housing 26, and inner lip 66 is located inside of outer lip 64 such that annular track 68 is created between outer lip 64 and inner lip 66. Located inside of inner lip 66 is annular sealing ring 70, and located inside of sealing ring 70 are locator pins 74, inlet port 80, flow channel 82 and flow channel outlet port 82B. In the embodiment depicted, two locator pins 74 extend downward from bottom surface 72 to create a necessary alignment with holes 60 in disc 28 such that through bore 62 is aligned with flow channel outlet port 82B. Sealing ring 70 is similar in structure to sealing ring 45 described above in that it has a height between approximately 0.005 and 0.015 inches (0.0127 and 0.0381 centimeters) and a width between approximately 0.015 and 0.025 inches (0.0381 and 0.0635 centimeters), although the invention is not so limited. Sealing ring 70 can assume any configuration capable of maintaining a proper seal with compensating disc 28. Flow channel 82 extends from inlet port 80 along bottom surface of puck 84 and bottom surface 72 of upper housing 26 to fluidly connect inlet port 80 to flow channel outlet port 82B. Ribs 76 protrude centrally from inner lip 66 at regular intervals, as do tabs 78, to aid in mating upper housing 26 to lower housing 24.

When compensating disc 28 is positioned atop surface 38 of lower housing 24 within flange 42, inner lip 66 of upper housing 26 is configured to slide over flange 42 and encapsulate compensating disc 28 inside internal chamber 29. More specifically, inner lip 66 of upper housing 26 rests on shoulder 42C of lower housing 24. Sealing ring 70 grips and thereby seals compensating disc 28 to bottom surface 72 of upper housing 26 to prevent leaks. To further secure compensating disc 28 into its predetermined location, locator pins 74 are received into holes 60 located on rim 56, thereby placing through bore 62 in fluid communication with inlet port 80. Even further still, centering ribs 76 center inner lip 66 of upper housing 26 with respect to an outer surface of flange 42 from lower housing 24. Boss 78A engages notch 43A and boss 78B engages notch 43B to ensure proper rotational alignment of middle housing 26 and lower housing 24. Channel 82 conducts fluid from inlet 30 to inlet port 80. Puck 84 is a convex protrusion extending centrally from bottom surface 72 around channel 82. So configured, upper housing 26 forms a top portion of internal chamber 29, which houses compensating disc 28.

Dimensions

Figure 6:
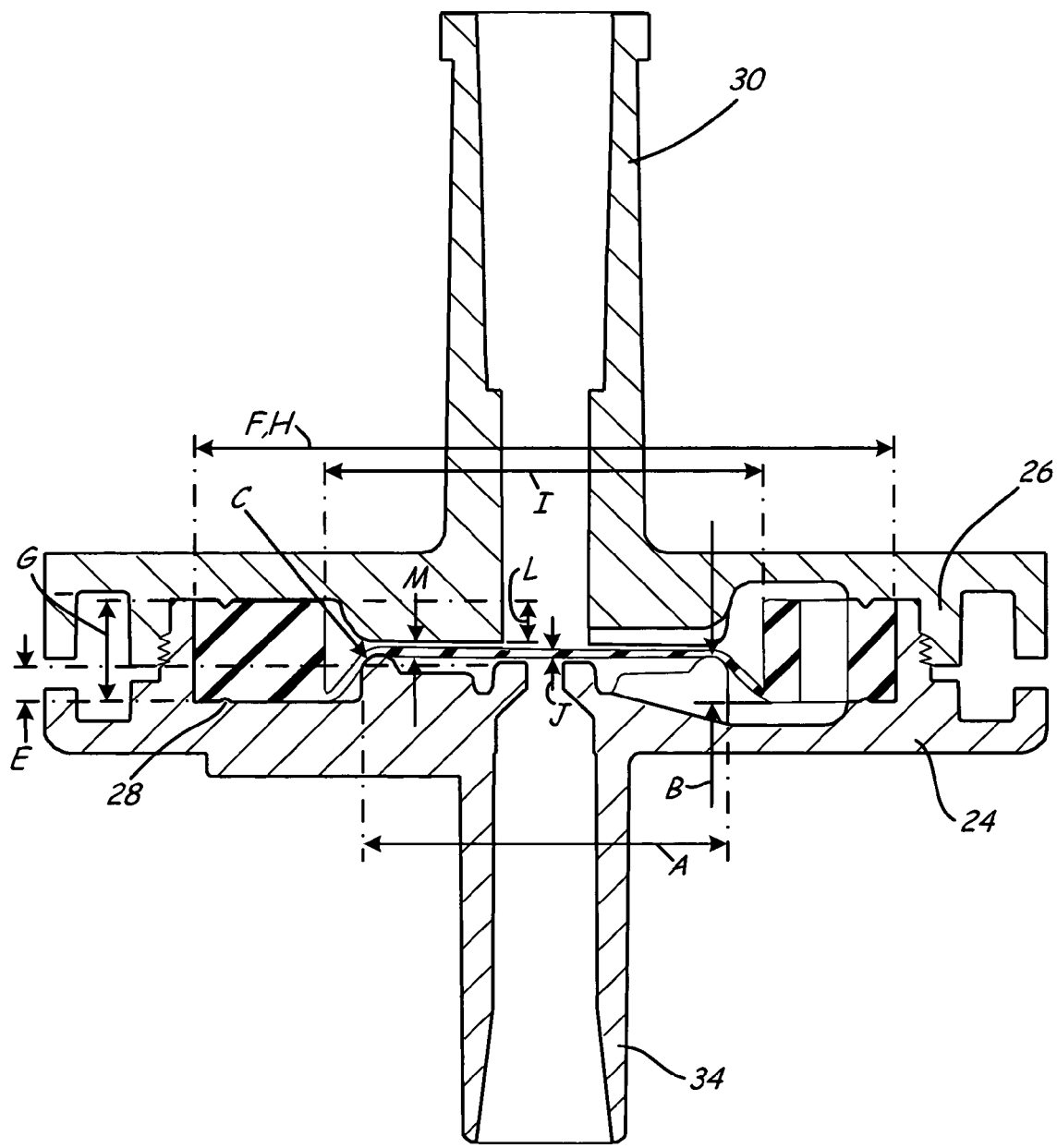
FIG. 6 is a cross section of the pressure compensating device from FIG. 2 assembled.

FIG. 6 is a cross section of compensating device 12 from FIG. 2 fully assembled for use in IV therapy administration system 10. Depicted in FIG. 6 are components of compensating device 12 described in detail above: lower housing 24, upper housing 26, compensating disc 28, inlet 30, and outlet 34. Also labeled in FIG. 6 are dimensions A-N, which can be used to manufacture the depicted embodiment of compensating device 12.

In the depicted embodiment, lower housing 24 has approximately the following dimensions. Land 50 has diameter A between about 0.450 inches (1.14 cm) and about 0.460 inches (1.17 cm), more preferably between about 0.454 inches (1.15 cm) and about 0.457 inches (1.16 cm). Land 50 has height B between about 0.050 inches (0.127 cm) and about 0.060 inches (0.152 cm), more preferably between about 0.053 inches (0.135 cm) and about 0.057 inches (0.145 cm). The raised portion of land 50 has radius C between about 0.010 inches (0.025 cm) and about 0.030 inches (0.077 cm), more preferably between about 0.020 inches (0.051 cm) and about 0.025 inches (0.064 cm). Outlet port ring 49 has height E between about 0.047 inches (0.120 cm) to about 0.057 inches (0.145 cm), more preferably between about 0.049 inches (0.124 cm) and 0.054 inches (0.137 cm). Flange 42 has inner diameter F between about 0.875 inches (2.22 cm) and about 0.885 inches (2.25 cm), more preferably between about 0.879 inches (2.23 cm) and about 0.882 inches (2.24 cm).

In the depicted embodiment, compensating disc 28 has approximately the following dimensions. Rim 56 has height G between about 0.134 inches (0.340 cm) and about 0.144 inches (0.366 cm), more preferably between about 0.136 inches (0.346 cm) and about 0.142 inches (0.361 cm). Rim 56 has outer diameter H between about 0.867 inches (2.20 cm) and about 0.877 inches (2.23 cm), more preferably between about 0.870 inches (2.21 cm) and about 0.875 inches (2.22 cm). Rim 56 has inner diameter I between about 0.505 inches (1.28 cm) and about 0.520 inches (1.32 cm), more preferably between about 0.510 inches (1.30 cm) and about 0.515 inches (1.31 cm). Diaphragm 58 has a thickness J between about 0.008 inches (0.020 cm) and about 0.020 inches (0.051 cm), more preferably between about 0.010 inches (0.025 cm) and about 0.016 inches (0.041 cm). Compensating disc 28 can be fabricated by compression molding using a silicone material having approximately the following material characteristics: durometer (Shore A) 50 and above (ASTM D-2240), tensile strength 1100 to 1200 (ASTM D-412), elongation percent 200-300 (ASTM D-412), modulus at 100 percent 60 to 70 (ASTM D-624), tear strength 50 to 60 (ASTM D-624), and Bayshore resilience 60 and above (ASTM D-624).

In the depicted embodiment, upper housing 26 has approximately the following dimensions. Puck 84 has height L between about 0.055 inches (0.140 cm) and about 0.065 inches (0.165 cm), more preferably between about 0.057 inches (0.145 cm) and about 0.061 inches (0.155 cm). Distance M between puck 84 and land 50 is between about 0.005 inches (0.013 cm) and about 0.040 inches (0.102 cm), more preferably between about 0.010 inches (0.025 cm) and about 0.030 inches (0.076 cm).

The above recited dimensions are configured so that compensating device 12 maintains the pressure differential between inlet 30 and outlet 34. Painstaking research has resulted in the discovery that the dimensions of compensating disc 28 must relate to dimensions of internal chamber 29 within certain ratios in order to achieve improved accuracy of pressure compensating device 12. For example, rim 56 height G relative to land 50 height B has a ratio between about 2 and about 3. Rim 56 inner diameter I relative to land 50 outer diameter A has a ratio between about 1.10 and about 1.15. Land 50 height B relative to port ring 49 height E has a ratio between about 1.0 and about 1.1. A distance between about 0.015 inches (0.038 cm) and about 0.040 inches (0.102 cm) should span between a top surface of land 50 and a bottom surface of puck 84. Furthermore, rim 56 height G and inner diameter I are dimensioned relative to the distance between top surface 38 of lower housing 24 and puck 84 of upper housing 26. In other words, internal chamber 29 must have sufficient depth to allow diaphragm 58 to flex freely. Construction of pressure compensating device 12 with the above recited ratios has been shown to optimize the effectiveness of pressure compensation.

Operation

Compensating device 12 is designed to compensate for changes in pressure between fluid entering inlet 30 and fluid exiting outlet 34. In use, gravity pulls IV solution out of IV bag 14 through upper tubing 16 and into inlet 30. From inlet 30, fluid passes through inlet port 80, fills the upper chamber and is routed radially via flow channel 82 to flow channel outlet port 82B. Fluid then flows through bore 62 into flow channel 46, under bottom surface 54 of diaphragm 58 filling the lower chamber 29. Fluid then passes through outlet port 48 and through outlet 34. During operation fluid pressure is exerted upon top and bottom surfaces of diaphragm 58 such that flex point 59 flexes at some frequency and amplitude. Depending on the amount of fluid pressure exerted on top and bottom surfaces of diaphragm, flex point 59 flexes towards or away from outlet port 48. Fluid flows through outlet port 48 where gravity pulls the fluid out of outlet 34 through lower tubing 18 and into venipuncutre site 20 on patient 22.

During operation, the top surface of diaphragm 58 is at essentially the same pressure as IV bag 14, and the bottom surface of diaphragm 58 is at essentially the same pressure as venipuncture site 20. A decrease in head pressure reduces the amount of pressure exerted on top surface of diaphragm 58 relative to pressure exerted on bottom surface of diaphragm 58, thereby forcing diaphragm 58 of compensating disc 28 to either increase or decrease the frequency and amplitude at which diaphragm 58 oscillates towards or away from outlet 48 of lower housing 24. When diaphragm 58 moves away from outlet ring 49 it effectively increases space for fluid to enter outlet port 48, thereby increasing rate of fluid flow. The converse is also true such that an increase in head pressure results in a more obstructed outlet port 48 and a decreased rate of fluid flow. Compensating device 12 uses compensating disc 28 to maintain the pressure differential between the inlet 30 and outlet 34.

In order to optimize the functionality of compensating device 28 the components as outlined and depicted must be properly positioned relative to each other. For compensating disc 28 to function properly several components must be parallel. A top surface of land 50 is preferably parallel to a bottom surface of puck 84. Top surface 38 of lower housing 24 is also preferably parallel to bottom surface 72 of upper housing 26. Furthermore, a top surface of outlet ring 49 is preferably parallel to bottom surface 54 of diaphragm 58 when diaphragm 58 is not deflected by a pressure differential. Such parallelism, along with the dimensions described above, ensure that diaphragm 58 is stretched equally across land 50 and therefore, flex point 59 is aligned over a central axis of outlet port 48. When diaphragm 58 is engaged by land 50, it is neither too taut nor too loose and is free to flex or deflect maximally as fluid passes over top surface of diaphragm 58 and bottom surface of diaphragm 58 during operation.

Although the present invention has been described with reference to preferred embodiments, workers skilled in the art will recognize that changes may be made in form and detail without departing from the spirit and scope of the invention.

The invention claimed is:

1. A pressure compensating device comprising:
   a housing including an inlet port, an outlet port fluidly connected to the inlet port, an annular land surrounding the outlet port and an internal chamber located between the inlet port and the outlet port; and
   a compensating disc located within the internal chamber, the disc having a diaphragm with a centrally located flex point and a thick rim attached to and surrounding the diaphragm, wherein the diaphragm engages the land allowing the flex point to deflect freely above the outlet port, wherein a ratio of a height of the rim to a height of the annular land is between about 2.4 and about 2.59, and wherein a ratio of an inner diameter of the rim to an outer diameter of the annular land is between about 1.12 and about 1.13.

2. The pressure compensating device of claim 1, wherein the diaphragm stretches across the land to bring the flex point over a central axis of the outlet port.

3. The pressure compensating device of claim 1, wherein a top surface of the internal chamber and a bottom surface of the internal chamber are substantially parallel.

4. The pressure compensating device of claim 3, wherein the top surface of the internal chamber has a downwardly protruding puck, and wherein a bottom surface of the puck is substantially parallel to a top surface of the annular land.

5. The pressure compensating device of claim 4, wherein the outlet port is surrounded by a port ring, and wherein a top surface of the port ring is substantially parallel to a bottom surface of the diaphragm.

6. The pressure compensating device of claim 1, wherein a top surface of the internal chamber has a sealing ring for engaging a top surface of the disc and a bottom surface of the internal chamber has a sealing ring for engaging a bottom surface of the disc.

7. The pressure compensating device of claim 1, wherein the compensating disc and the housing are dimensioned relative to one another such that there is sufficient room within the internal chamber for the diaphragm to deflect freely.

8. The pressure compensating device of claim 1, wherein the outlet port is surrounded by a port ring, and wherein a ratio of a height of the annular land to a height of the port ring is between about 1.04 and about 1.09.

9. A pressure compensating device comprising:
a housing comprising:
- an upper housing section and a lower housing section;
- an inlet extending from the upper housing and an outlet extending from the lower housing;
- an internal chamber located between the upper housing and the lower housing;
- an inlet port located in the upper housing fluidly connecting the inlet to the chamber and an outlet port located in the lower housing fluidly connecting the outlet to the chamber;
- a port ring surrounding the outlet port, the port ring having a height; and
- an annular land surrounding the port ring, the land having an upper surface, an outer diameter and a height; and a compensating disc located within the internal chamber, the compensating disc comprising:
- a thick rim having a top surface, a side surface, a bottom surface, a height, an inner diameter and an outer diameter; and
- a diaphragm attached to the thick rim at the bottom surface and the inner diameter of the rim, the diaphragm having a top side, a bottom side, and a centrally located flex point aligned with the outlet port, wherein a ratio of the rim height relative to the land height is between about 2.4 and about 2.59, a ratio of the inner diameter of the rim relative to the outer diameter of the annular land is between about 1.12 and about 1.13, and a ratio of the land height relative to the port ring height is between about 1.04 and about 1.09 such that the diaphragm engages and stretches across the annular land equally thereby bringing the flex point in alignment with a central axis of the outlet port.

10. The pressure compensating device of claim 9, wherein a top surface of the internal chamber and a bottom surface of the internal chamber are substantially parallel.

11. The pressure compensating device of claim 10, wherein the top surface of the internal chamber has a downwardly protruding puck that is substantially parallel to the upper surface of the annular land, and wherein a top surface of the port ring is substantially parallel to bottom side of the diaphragm.

12. The pressure compensating device of claim 11, wherein the compensating disc comprises silicone.

13. The pressure compensating device of claim 12, wherein the diaphragm has a thickness between about 0.010 inches and about 0.016 inches.

14. The pressure compensating device of claim 12, wherein the compensating disc has a durometer hardness of at least 50.

15. The pressure compensating device of claim 9, wherein the upper surface of the annular land is substantially parallel to a top surface of the chamber.

16. The pressure compensating device of claim 9, wherein the upper housing and the lower housing both have sealing rings for engaging the compensating disc within the chamber and preventing leaks.

* * * * *